(12) United States Patent
Ho

(10) Patent No.: US 7,484,255 B2
(45) Date of Patent: Feb. 3, 2009

(54) MULTIFUNCTIONAL PILLOW

(76) Inventor: Ying-Chuan Ho, 235 Chung-Ho Box, 8-24 Taipei (TW)

( * ) Notice: Subject to any disclaimer, the term of this patent is extended or adjusted under 35 U.S.C. 154(b) by 0 days.

(21) Appl. No.: 11/935,411

(22) Filed: Nov. 6, 2007

(65) Prior Publication Data
US 2008/0256710 A1 Oct. 23, 2008

(30) Foreign Application Priority Data
Apr. 20, 2007 (TW) ............................... 96114158 A

(51) Int. Cl.
*A47G 9/10* (2006.01)
(52) U.S. Cl. .................. 5/636; 5/640; 5/643; 5/915
(58) Field of Classification Search ............... 5/636, 5/639, 640, 643, 645, 108, 109, 915; 368/10, 368/12
See application file for complete search history.

(56) References Cited

U.S. PATENT DOCUMENTS

| | | | | |
|---|---|---|---|---|
| 4,941,478 A * | 7/1990 | Takeuchi et al. | ............ | 128/848 |
| 5,144,600 A * | 9/1992 | Cheng | .......................... | 368/12 |
| 6,081,949 A * | 7/2000 | Delicia | .......................... | 5/639 |
| 6,189,167 B1 * | 2/2001 | Tsai | .............................. | 5/636 |
| 6,236,621 B1 * | 5/2001 | Schettino | ..................... | 368/10 |
| 6,386,201 B1 * | 5/2002 | Fard | .......................... | 128/848 |
| 7,266,047 B2 * | 9/2007 | Chan | ............................. | 368/10 |

FOREIGN PATENT DOCUMENTS

GB 2208003 A * 2/1989

* cited by examiner

*Primary Examiner*—Michael Trettel

(57) ABSTRACT

A multifunctional pillow, comprises a cover including an upper cover, a lower cover and a top cover; a sliding track assembly installed between the upper cover and the lower cover; tile sliding track assembly including an upper frame and a lower frame; the upper frame being embedded into the upper cover; a bearing being installed in the upper cover; the lower frame having a trench; in assembling, the bearing being placed into the trench so that the bearing is slidable in the trench; and a control panel installed in the cover; an interior of the control panel having a control circuit board; the control circuit board being connected to the motor, a microswitch, an audio sensor, a trumpet, and a vibrator; one end of the microswitch being connected to a touch panel and another end thereof being connected to a control circuit board.

8 Claims, 5 Drawing Sheets

MULTIFUNCTIONAL PILLOW

FIELD OF THE INVENTION

The present invention relates to pillows, and particularly to a multifunctional pillow which causes the user to stop snore and has the function of awaking the user effectively.

BACKGROUND OF THE INVENTION

The prior art pillow is installed with a vibrator which includes a base, a motor, a spindle, a crank, a sliding unit, a first sliding block, a second sliding block, a first sliding rod, a second sliding rod, a first frame, a second frame, an upper mask. The motor is fixed to the base. The spindle of the motor is eccentrically connected to the crank. The sliding unit is connected to another eccentric side of the crank. The sliding unit can move longitudinally in a guide groove of the second sliding block, The two frames are fixed to the base. The area of the two frames of the base has the two sliding rods. The first sliding block is supported by the two sliding rods and is moves leftwards or rightwards. When the motor receives control signals and then rotates, the spindle will drive the crank to rotate. The crank will drive the sliding unit to move around a circle, but since one end of the sliding unit is in the guiding groove of the first sliding block so that it only moves longitudinally in the guide groove so as to drive the first sliding block to move leftwards and rightwards. The first sliding block is firmly secured to the upper mask and the second sliding block is also firmly secured to the upper mask. Therefore, when the first sliding block vibrates leftwards and rightwards, the upper mask vibrates leftwards and rightwards. The upper mask will drive the second sliding block to move so that the whole upper mask vibrates leftwards and rightwards.

The above mentioned prior art pillow has the defects that the components are very complicated. After it is used for a long time, it will be destroyed. In moving leftwards and rightwards, by the sliding unit moves in the guide groove, the sliding rod connected to the first sliding block will move leftwards and rightwards. Therefore, the sliding unit will collide the first sliding block so as to emit noise to affect the sleeping of the user.

SUMMARY OF THE INVENTION

Accordingly, the primary object of the present invention is to provide a multifunctional pillow which causes the user to stop snore and has the function of awaking the user effectively.

To achieve above objects, the present invention provides a multifunctional pillow, comprising: a cover including an upper cover, a lower cover and a top cover; the upper cover having a hole; the hole being engaged with an protrusion of the lower cover; the protrusion being a hollow receiving space for receiving a motor; a rotor of the motor being connected to an eccentric shaft; the eccentric shaft combined with a transfer rod; each of two ends of the transfer rod having a respective shaft units; one shaft unit being connected to the eccentric shaft and another shaft unit being connected to a buckle of the upper cover; a sliding track assembly installed between the upper cover and the lower cover; the sliding track assembly including an upper frame and a lower frame; the upper frame being embedded into the upper cover; a bearing being installed in the upper cover; the lower frame having a trench; in assembling, the bearing being placed into the trench so that the bearing is slidable in the trench; and a control panel installed in the cover; an interior of the control panel having a control circuit board; the control circuit board being connected to the motor, a microswitch, an audio sensor, a trumpet, and a vibrator; one end of the microswitch being connected to a touch panel and another end thereof being connected to a control circuit board; when the touch panel is pressed, the microswitch will be actuated so as to transfer signals to the control circuit board and thus the pillow is actuated.

The various objects and advantages of the present invention will be more readily understood from the following detailed description when read in conjunction with the appended drawing.

DETAILED DESCRIPTION OF THE INVENTION

In order that those skilled in the art can further understand the present invention, a description will be provided in the following in details. However, these descriptions and the appended drawings are only used to cause those skilled in the art to understand the objects, features, and characteristics of the present invention, but not to be used to confine the scope and spirit of the present invention defined in the appended claims.

Figure 1:
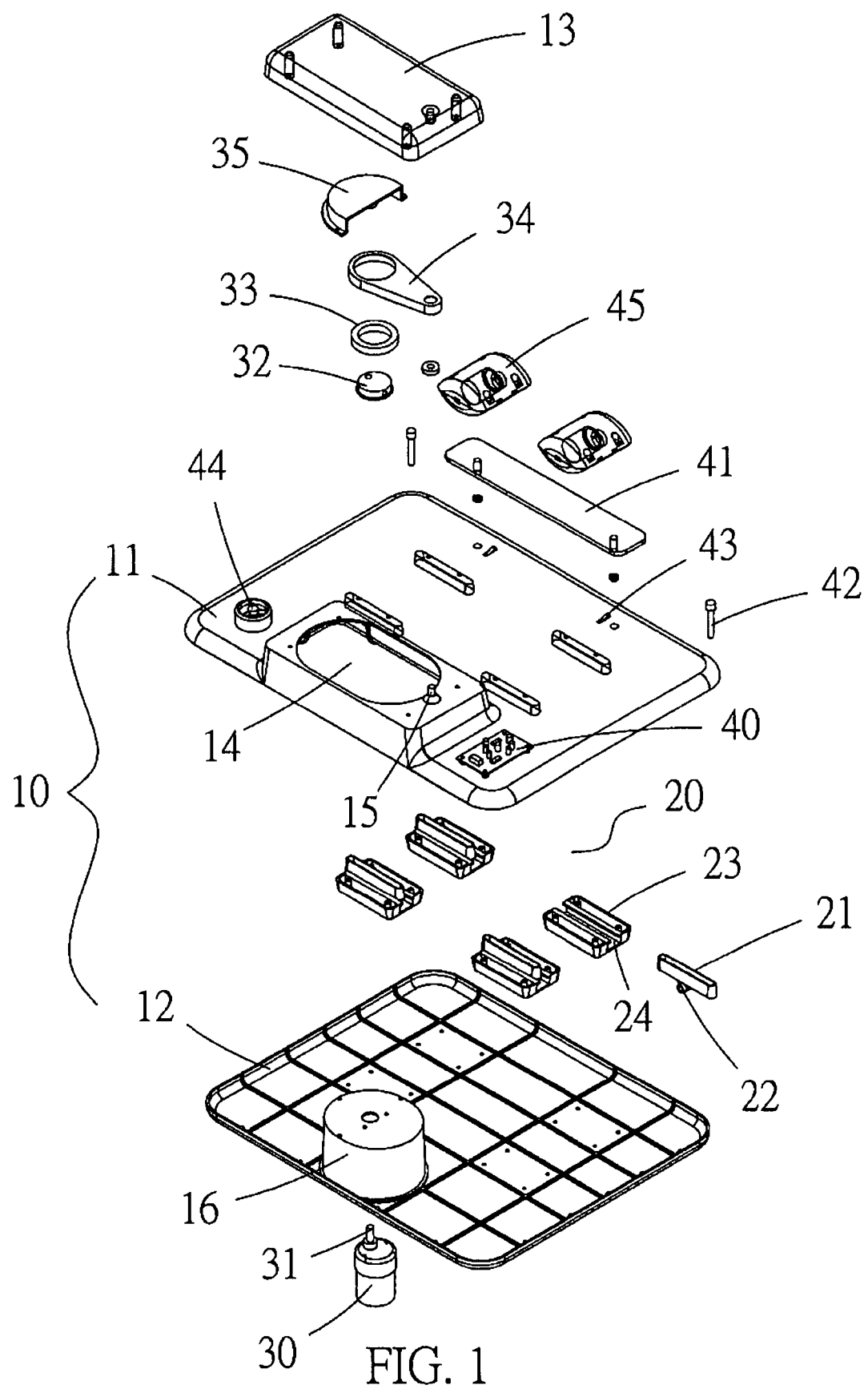
FIG. 1 is an exploded perspective view of the present invention.

Referring to FIG. 1, the multifunctional pillow of the present invention is illustrated. The present invention has the following elements.

A cover 10 includes an upper cover 11, a lower cover 12 and a top cover 13.

The upper cover 11 has a hole 14. The hole 14 is engaged with a protrusion 16 of the lower cover 12. The protrusion 16 is a hollow receiving space for receiving a motor 30. A rotor 31 of the motor 30 is connected to an eccentric shaft 32. The eccentric shaft 32 is combined with a transfer rod 34. Each of two ends of the transfer rod 34 has a respective shaft units 33. One shaft unit 33 is connected to the eccentric shaft 32 and another shaft unit 33 is connected to a buckle 15 of the upper cover 11.

A sliding track assembly 20 is installed between the upper cover 11 and the lower cover 12. The sliding track assembly 20 includes an upper frame 21 and a lower frame 23. The upper frame 21 is embedded into the upper cover 11. A bearing 22 is installed in the upper cover 11. The lower frame 23 has a trench 24. In assembling, the bearing 22 is placed into the trench 24 so that the bearing 22 is slidable in the trench 24.

Figure 2:
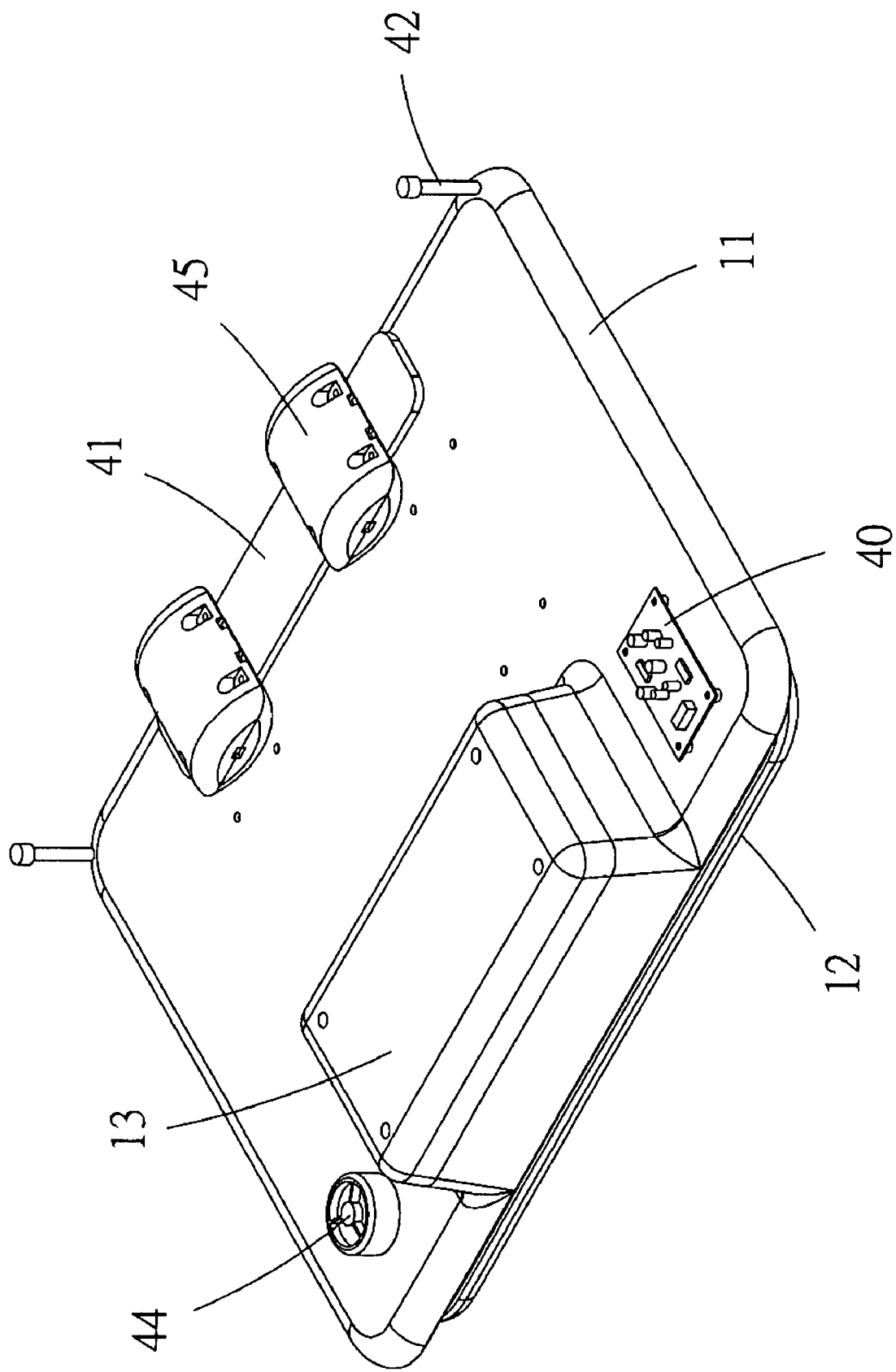
FIG. 2 is an assembled view of the present invention.

Referring to FIG. 2, the assembled perspective view of the present invention is illustrated. A control panel 40 is installed in the cover 10. An interior of the control panel 40 has a control circuit board. The control circuit board is connected to the motor 30, a microswitch 43, an audio sensor 42, a trumpet 44, and a vibrator 45. One end of the microswitch 43 is connected to a touch panel 41 and another end thereof is connected to a control circuit board. When the touch panel is pressed, the microswitch 43 will be actuated so as to transfer signals to the control circuit board and thus the pillow is actuated.

Moreover, a control panel 40 is built with a snore stop mode and an alarm mode. The alarm mode further has a first mode, a second mode, a third mode, an over-sleeping-proof mode. The first mode provides the pillow to emit alarm sound. The second mode serves to generate vibrations through the vibrator. The third mode causes that the alarm sounds and vibration are generated at the same time. The over-sleeping-proof mode can be performed with the first, second or third mode.

Figure 3:
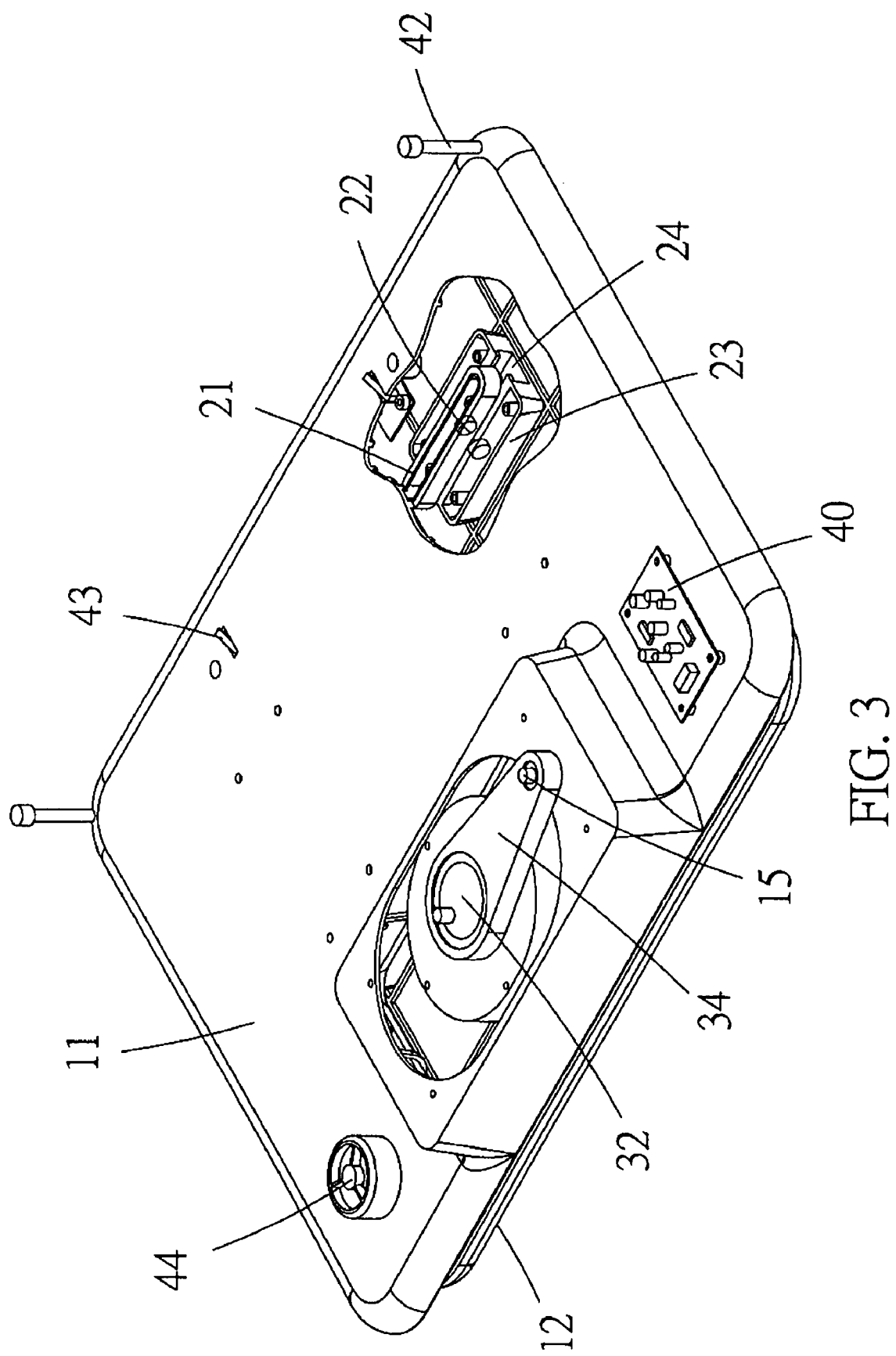
FIG. 3 is a perspective view showing that the sliding track of the present invention is assembled to the cover.

Referring to FIG. 3, the sliding track assembly of the present invention is illustrated. The sliding track assembly is installed between the upper cover 11 and the lower cover 12. When the upper cover 11 moves leftwards or rightwards, the bearing 22 of the sliding track assembly 20 is in the trench 24 so as to drive the upper cover 11 to move easily. Therefore, it has a silent effect.

Figure 4:
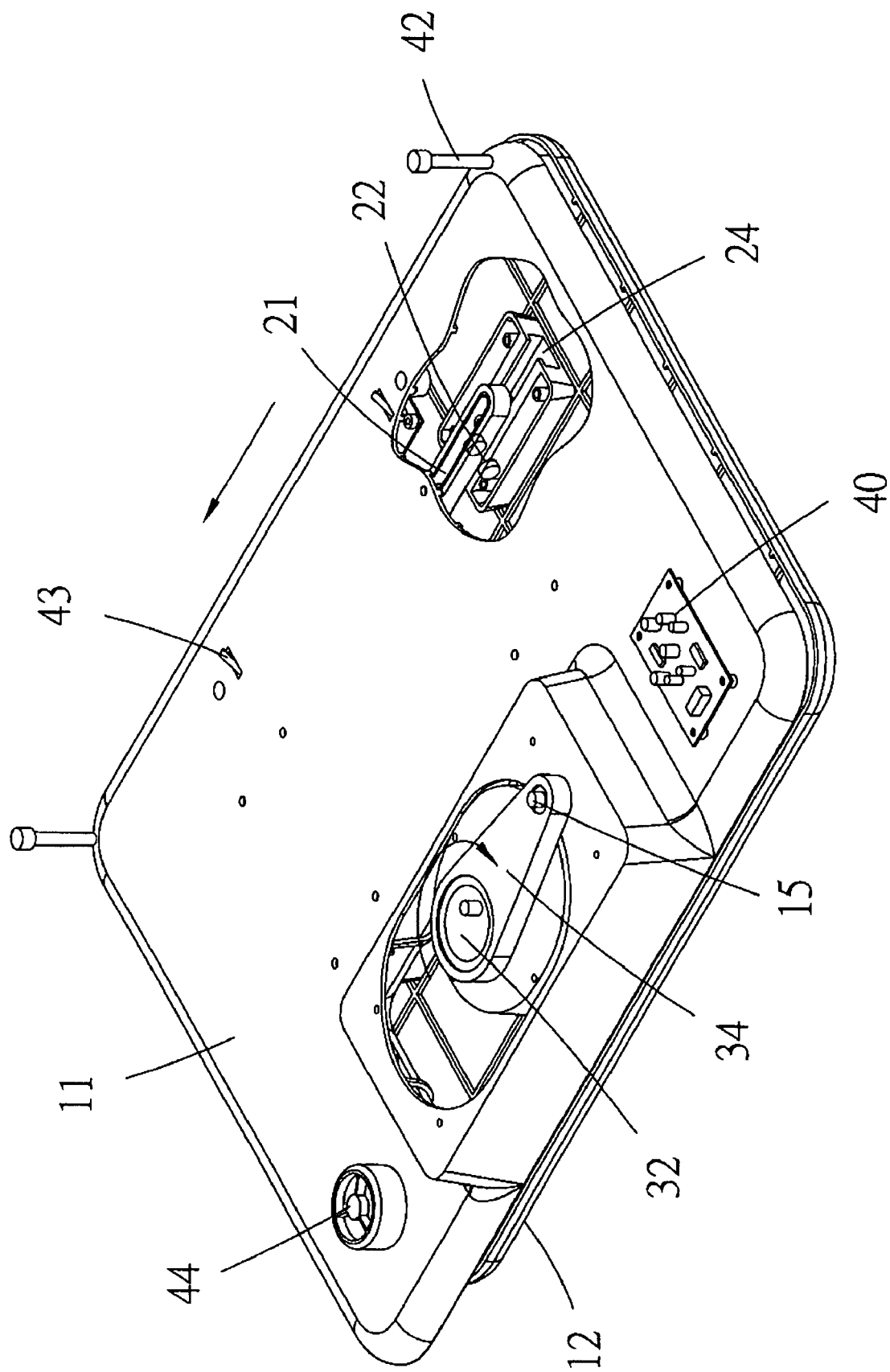
FIG. 4 is schematic view showing the operation of the present invention.

Referring to FIG. 4, the operation of the present invention is illustrated. When the snore stop mode is actuated, the audio sensor 42 will detect snore sound. If the snore sound is too noisy, the processor of the control circuit board will rotate the motor 30 so that the eccentric shaft 32 of the motor 30 drives the transfer rod 34 to as to make the upper cover 11 swing slight. This will prevent the user from snore so as to affect others.

In the alarm mode of the present invention, it is like the conventional alarm clock. When it is at a setting time, the alarm sound is emitted so as to wake up the user. The alarm clock is installed at one side of the upper cover to more close the user. If not to interfere other people nearby, a vibrator can be used. Moreover, the alarm and vibrator can be used at the same time. When a setting time is achieved, the trumpet 44 will emit sound or the vibrator will vibrate. When the user leaves away from the pillow, the touch panel 44 is returned to stop the alarm clock or the vibrator.

If the user stops the alarm clock and sleeps again, the over-sleeping-proof mode is actuated. If the user lies upon the pillow again in a period of 15 minutes after the user leaves from the pillow first time, the alarm clock or the vibrator will be actuated after 5 minutes.

In the over-sleeping-proof mode, the upper cover 11 is installed with the touch panel 41. The microswitch 43 is installed at a lower side of the touch panel 41. In sleeping, the head of the user will press the touch panel 41, the touch panel 41 will press the microswitch 43 to be at a turning on state. When it is at the setting awaking time, the head leaves from the cover so that the touch panel 41 will not press the microswitch 43 again, the microswitch 43 is in a turning off state. The alarm clock stops. Because the user's head has left from the cover so the user is awaked.

Figure 5:
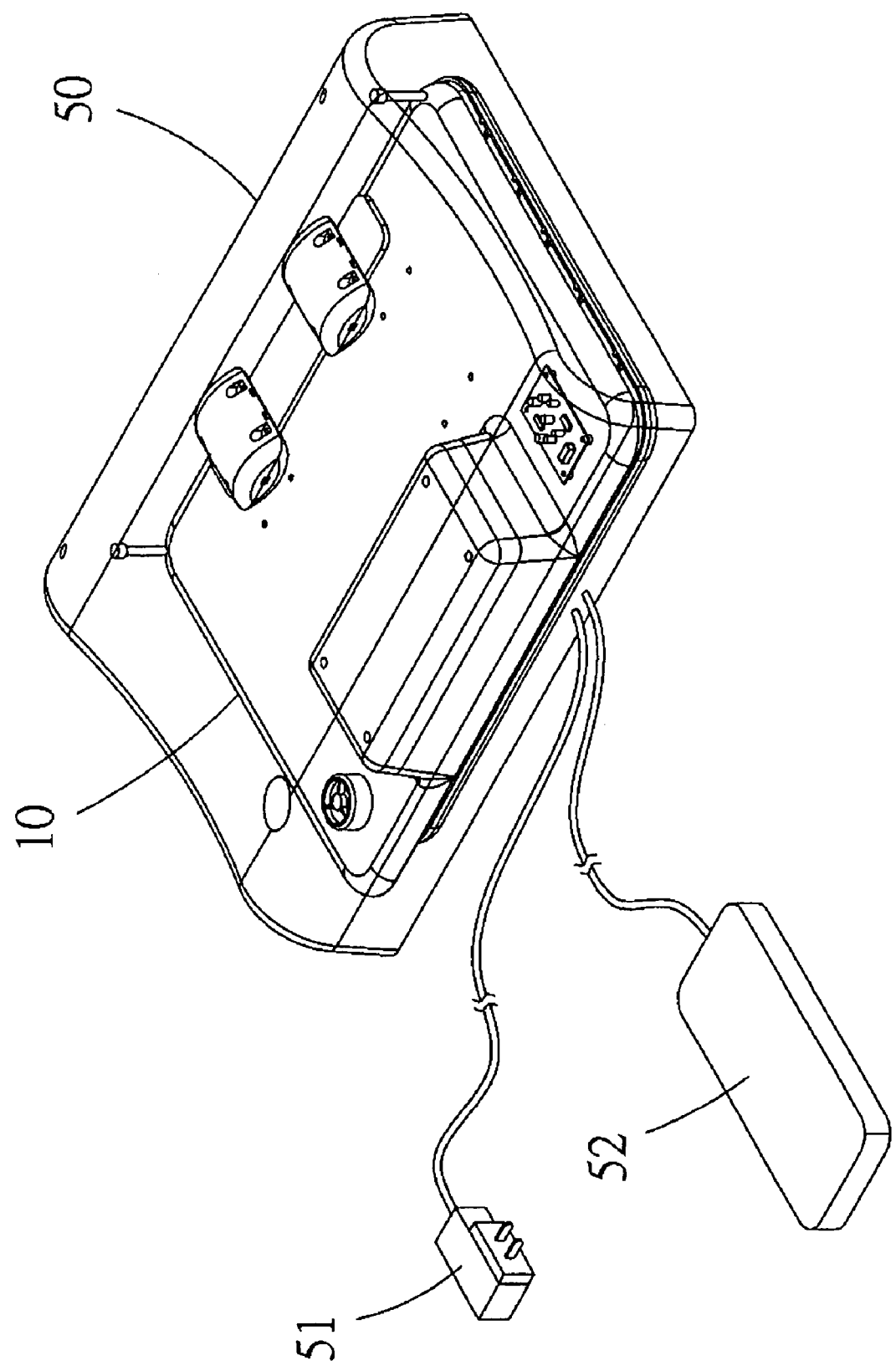
FIG. 5 shows the embodiment of the present invention.

With referring to FIG. 5, a foam pillow 50 is installed on the upper cover 11. The foam pillow 50 is ergonomic. When the user lies upon the pillow, the user will feel comfortable. Furthermore, the pillow has a beautiful outlook. One end of the cover 10 is connected to a transformer 51 and a keyboard 52. The transformer 51 provides direct current to the control panel 40. The keyboard 52 serves to set the control panel 40.

Advantages of the present invention are that the present invention is a personal design which provides the user to stop snore in sleeping and the alarm clock will wake up the user as the user in sleep.

Furthermore, the control panel is set with a snore stop mode and an alarm mode and the alarm mode further has a first, a second and a third modes and an over-sleep-proof mode. The various modes causes the user to select a desire one for using.

Furthermore, the present invention has a concrete mode by using a sliding track to increase the tolerant of the device. The sliding track includes an upper frame and a lower frame. The upper frame is engaged to the upper cover. The upper frame is installed with a bearing. The lower frame has a trench so that the bearing is slidable in the trench.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A multifunctional pillow, comprising:
   a cover including an upper cover, a lower cover and a top cover;
   the upper cover having a hole; the hole being engaged with an protrusion of the lower cover; the protrusion being a hollow receiving space for receiving a motor; a rotor of the motor being connected to an eccentric shaft; the eccentric shaft combined with a transfer rod; each of two ends of the transfer rod having a respective shaft units; one shaft unit being connected to the eccentric shaft and another shaft unit being connected to a buckle of the upper cover;
   a sliding track assembly installed between the upper cover and the lower cover; the sliding track assembly including an upper frame and a lower frame; the upper frame being embedded into the upper cover; a bearing being installed in the upper cover; the lower frame having a trench; in assembling, the bearing being placed into the trench so that the bearing is slidable in the trench; and
   a control panel installed in the cover; an interior of the control panel having a control circuit board; the control circuit board being connected to the motor, a microswitch, an audio sensor, a trumpet, and a vibrator; one end of the microswitch being connected to a touch panel and another end thereof being connected to a control circuit board; when the touch panel is pressed, the microswitch will be actuated so as to transfer signals to the control circuit board and thus the pillow is actuated.

2. The multifunctional pillow as claimed in claim 1, wherein the pillow is a foam pillow installed on the upper cover; the foam pillow is ergonomic; when the user lies upon the pillow, the user will feel comfortable.

3. The multifunctional pillow as claimed in claim 1, wherein one end of the cover is connected to a transformer and a keyboard; the transformer provides direct current to the control panel and the keyboard serves to set the control panel.

4. The multifunctional pillow as claimed in claim 1, wherein the control panel is built with a snore stop mode and an alarm mode.

5. The multifunctional pillow as claimed in claim 4, wherein in the alarm mode; when it is at a setting time, the alarm sound is emitted or a vibrator vibrates so as to wake up the user; when the user leaves away from the pillow, the touch panel is returned to stop the alarm clock or the vibrator.

6. The multifunctional pillow as claimed in claim 4, wherein the alarm mode further has a first mode, a second mode, a third mode, an over-sleeping-proof mode; the first mode provides the pillow to emit alarm sound; the second mode serves to generate vibrations through the vibrator; the third mode causes that the alarm sounds and vibration are generated at the same time; and the over-sleeping-proof mode can be performed with the first, second or third mode.

7. The multifunctional pillow as claimed in claim 6, wherein if the user stops the alarm clock and sleeps again, the over-sleeping-proof mode is actuated; in the over-sleeping-proof mode, if the user lies upon the pillow again in a period of 15 minutes after the user leaves from the pillow first time, the alarm clock or the vibrator will be actuated after 5 minutes.

8. The multifunctional pillow as claimed in claim 4, wherein when the snore stop mode is actuated, the audio sensor will detect snore sound; if the snore sound is too noisy, the processor of the control circuit board will rotate the motor so that the eccentric shaft of the motor drives the transfer rod to as to make the upper cover swing slight; and this will prevent the user from snore so as to affect others.

* * * * *